United States Patent [19]

Ivers et al.

[11] Patent Number: 5,339,810

[45] Date of Patent: Aug. 23, 1994

[54] PULSE OXIMETRY SENSOR

[75] Inventors: David L. Ivers, Jupiter; Stanley R. Mach, Palm Beach Gardens, both of Fla.

[73] Assignee: Marquette Electronics, Inc., Milwaukee, Wis.

[21] Appl. No.: 56,512

[22] Filed: May 3, 1993

[51] Int. Cl.⁵ .............................................. A61B 5/00
[52] U.S. Cl. ...................................... 128/633; 128/664; 128/665
[58] Field of Search .......................... 128/633–634, 128/664–667; 356/39–41

[56] References Cited

U.S. PATENT DOCUMENTS

| | | | |
|---|---|---|---|
| 3,638,640 | 2/1972 | Shaw . | |
| 4,510,938 | 4/1985 | Jobois et al. | 128/833 |
| 4,611,600 | 9/1986 | Cohen | 128/667 |
| 4,636,636 | 1/1987 | McMahon et al. | 250/227 |
| 4,684,245 | 8/1987 | Goldring | 356/41 |
| 4,685,464 | 8/1987 | Goldberger et al. | 128/633 |
| 4,690,492 | 9/1987 | Beard | 350/96.20 |
| 4,736,100 | 4/1988 | Vastagh | 250/227 |
| 4,761,047 | 8/1988 | Mori | 350/96.1 |
| 4,776,339 | 10/1988 | Schreiber | 128/633 |
| 4,830,014 | 5/1989 | Goodman et al. | 128/665 |
| 4,867,165 | 9/1989 | Noller et al. | 128/633 |
| 4,883,055 | 11/1989 | Merrick | 128/633 |
| 4,913,150 | 4/1990 | Cheung et al. | 128/633 |
| 4,938,218 | 7/1990 | Goodman et al. | 128/633 |
| 4,944,568 | 7/1990 | Danbach et al. | 350/96.20 |
| 4,964,408 | 10/1990 | Hink et al. | 128/633 |
| 4,972,074 | 11/1990 | Wright | 250/227.11 |
| 4,974,929 | 12/1990 | Curry | 350/96.29 |
| 4,982,083 | 1/1991 | Graham et al. | 250/227.11 |
| 4,993,803 | 2/1991 | Suverison et al. | 350/96.20 |
| 5,007,704 | 4/1991 | McCartney | 350/96.21 |
| 5,035,243 | 7/1991 | Muz | 128/687 X |
| 5,054,488 | 10/1991 | Muz | 128/633 |
| 5,069,213 | 12/1991 | Polczynski | 128/633 |
| 5,088,493 | 2/1992 | Giannini et al. | 128/633 |
| 5,090,410 | 2/1992 | Saper et al. | 128/633 |
| 5,140,989 | 8/1992 | Lewis et al. | 128/665 |
| 5,170,786 | 12/1992 | Thomas et al. | 128/665 X |
| 5,209,230 | 5/1993 | Swedlow et al. | 128/664 X |

OTHER PUBLICATIONS

A New Light Shines in MRI, Nonin Medical, Inc. Biomedical Technology Information Service, vol. 18, No. 18, Nov. 15, 1990.

8604FO Pulse Oximeter with Fiber Optic Sensor for MRI, Nonin Medical, Inc. 1991.

*Primary Examiner*—Angela D. Sykes
*Attorney, Agent, or Firm*—Michael, Best & Friedrich

[57] ABSTRACT

An oximetry sensor constructed including first and second opposed shell members for engaging the opposite sides of a patient's finger. A coupler releasably connects a pair of LEDs to the first member for projecting light through the finger and a light detector is mounted on the other member for detecting unabsorbed light transmitting through the finger. One of the shell members is mounted for sliding movement on the other for engaging the opposite sides of the patients finger and a coupler retains the shell members in position. In a first embodiment, the LED's are directly releasably coupled to the first member and in a second embodiment a fiber optic cable releasably couples the LED's to the first member.

20 Claims, 5 Drawing Sheets

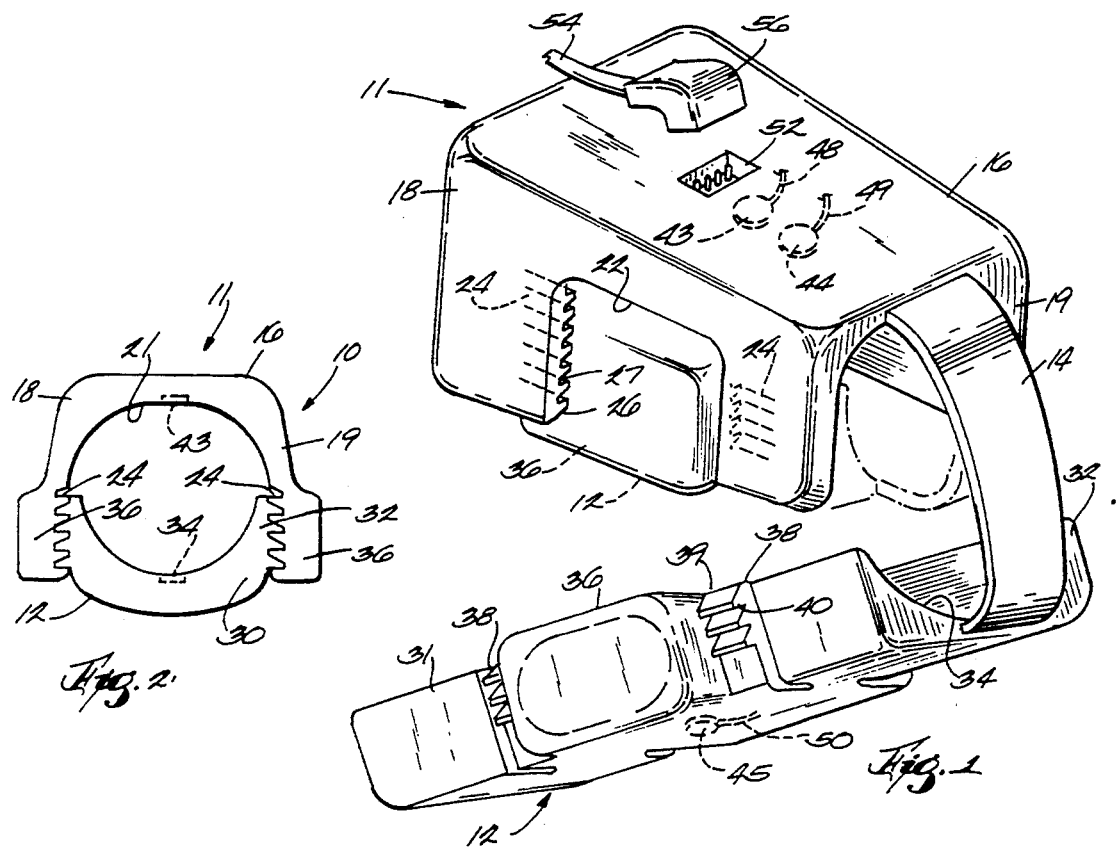
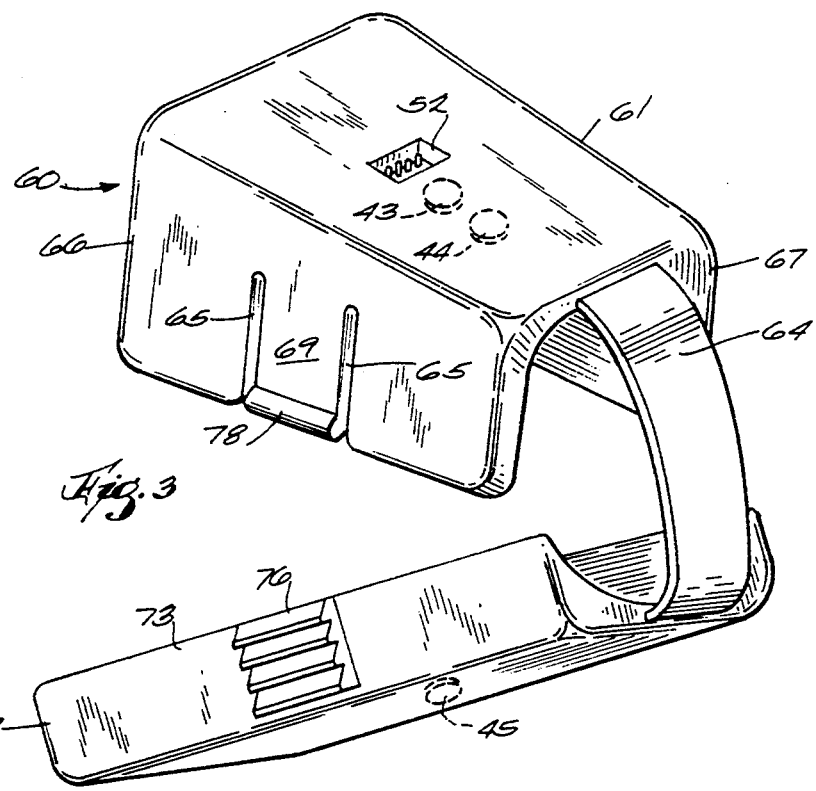

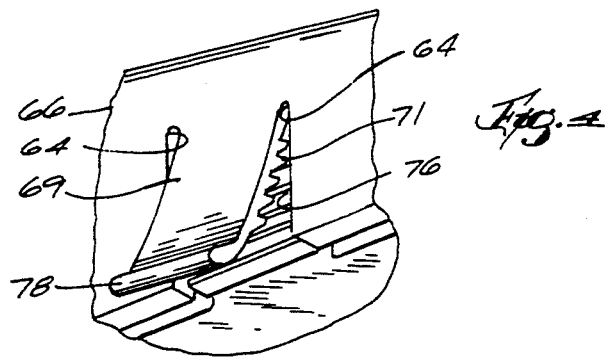
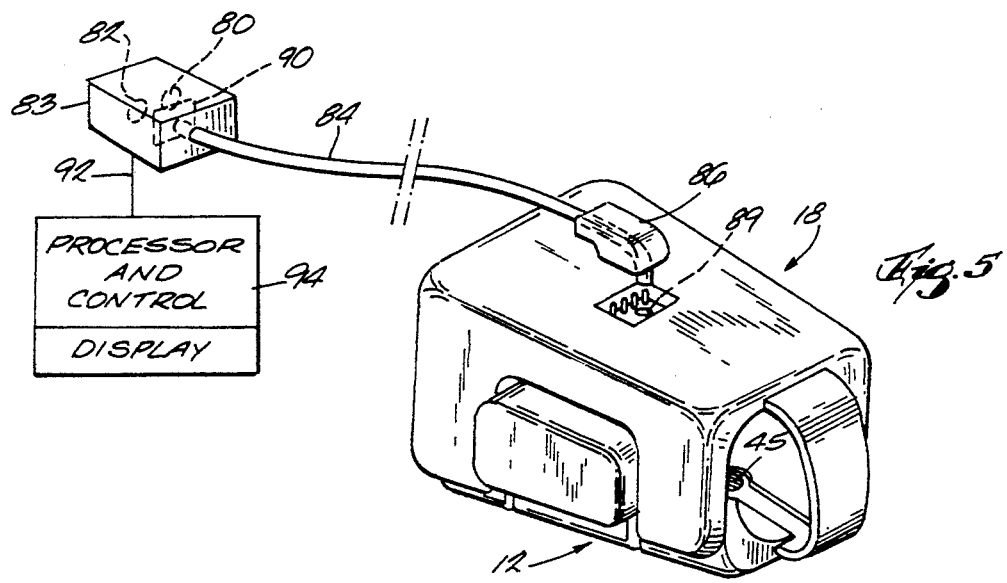
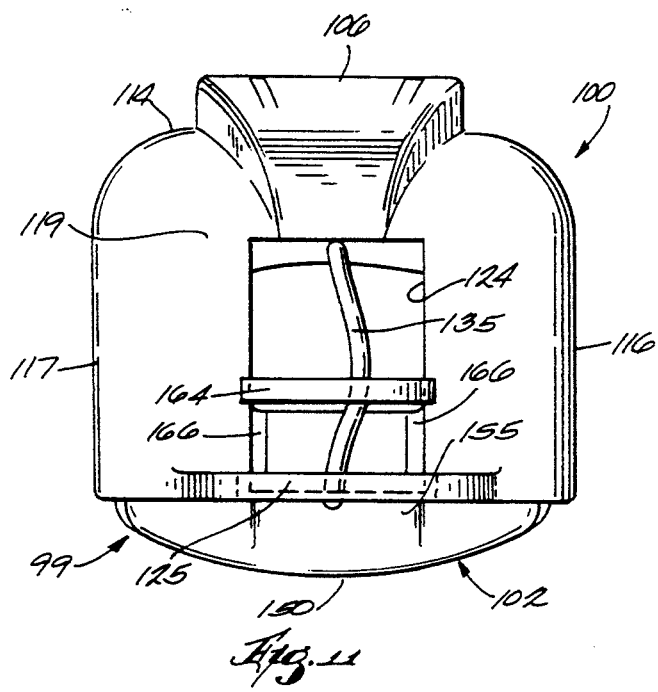
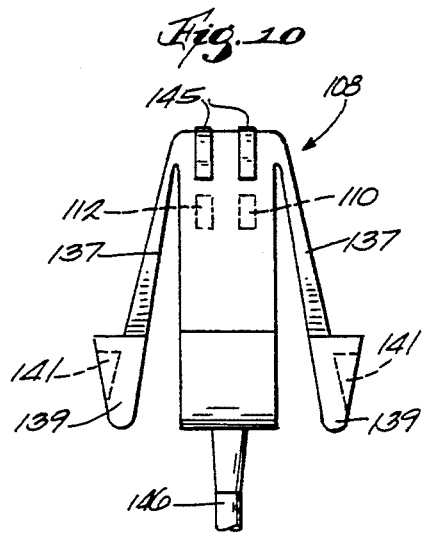

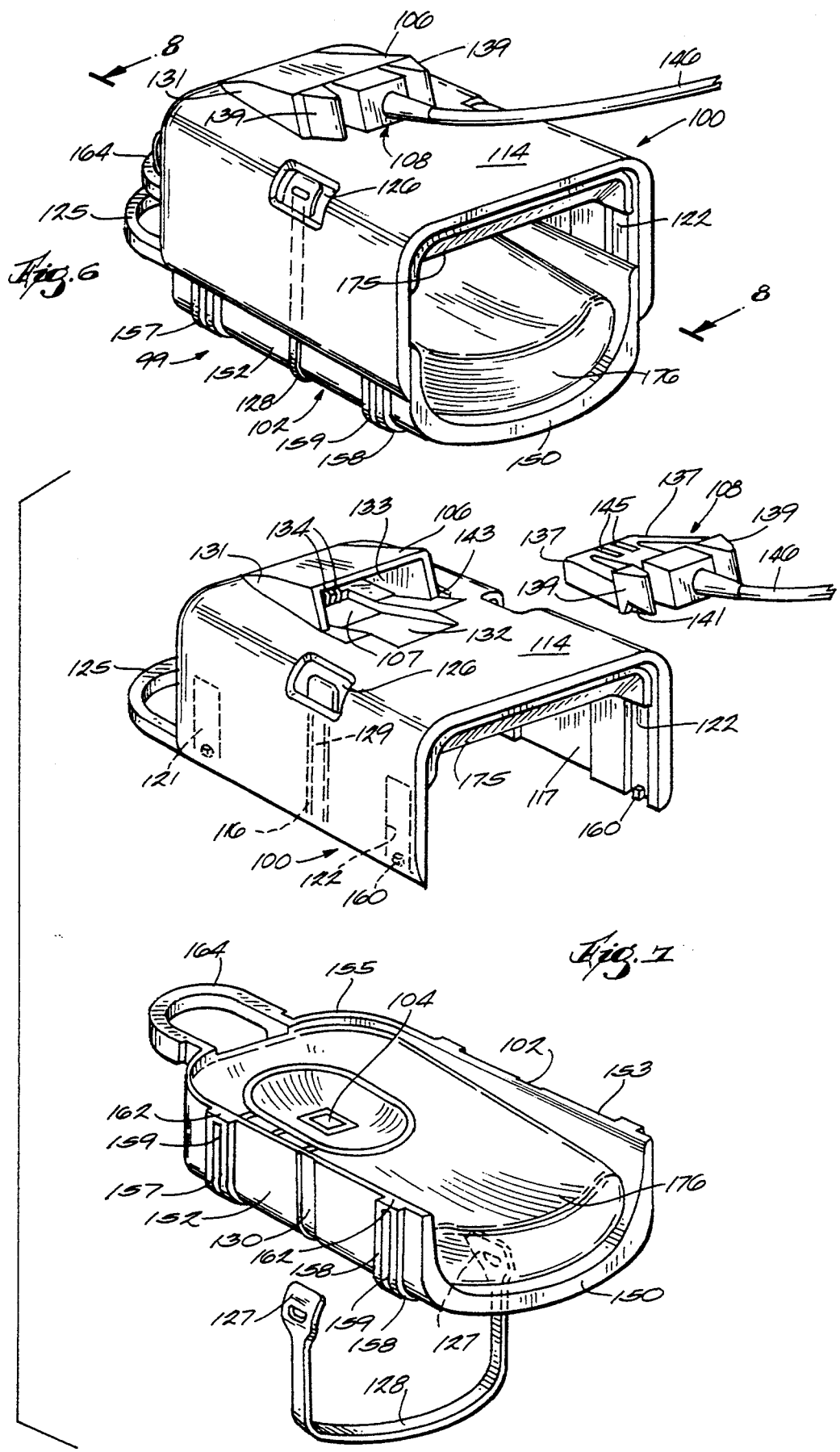

PULSE OXIMETRY SENSOR

BACKGROUND OF THE INVENTION

This invention relates to the measurement of oxygen saturation level of hemoglobin in arterial blood and more particularly to a non-invasive oximetry sensor.

Non-invasive oximeter commonly take advantage of the difference in the light absorption coefficient of hemoglobin and hemoglobin oxide with respect to light in the red and infrared ranges. This type of oximeter normally includes sensors that are placed against patient tissue which is well perfused and include sources for emitting light at one or more wavelengths into the tissue and a light detector for detecting the amount of light which passes through the tissue. The amount of light absorbed at each wavelength is used to calculate oxygen saturation in the patient's blood in accordance with Lambert-Beer's law. Such sensors are normally placed on the fingertip, earlobe, nasal septum, or forehead of the patient and preferably include means for retaining the sensor in position for the extended periods during which such measurements are made. Notwithstanding the requirement for durability, the probes are preferable disposable so as to insure sterility.

One type of oximeter sensor includes an adhesive strip for holding the LEDs and detector against the patient's tissue. Mother type includes a spring-biased clamp for attaching the sensor in position. The use of these probes involves considerable expense because the relatively costly LED's are integrally mounted in the disposable portion of the probe. In addition, while these methods of attachment have been effective for retaining the LEDs and detector in position, they tend to become uncomfortable if worn for extended period.

The Lambert-Beer's law for calculating blood oximetry employs coefficients which are dependent upon the wavelength of the light being emitted by the specific LEDs in the sensor. However, due to manufacturing tolerances, the wavelengths light emitted by LEDs used in oximetry sensors varies widely about some nominal value. Therefore, the accuracy of the oximetry measurements may suffer greatly unless the LEDs are carefully sorted to insure wavelengths within a narrow band width or the processor is reprogrammed for each successive oximeter sensor. However, reprogramming is impractical since the sensors are discarded after each use. One solution to these problems is disclosed in U.S. Pat. No. 4,700,208 and involves sorting the LEDs into narrow band-width ranges and providing a coding resistor in each sensor which advises the processor the specific wavelengths of the particular LEDs in that sensor. The processor then determines the appropriate coefficients to De used in the oximeter calculation from a lookup table. While this latter method has been commercially successful, the requirement for sorting and the need for a coding resistor increase the cost of manufacturing the sensors.

SUMMARY OF THE INVENTION

It is an object of the invention to provide a new and improved oximetry sensor.

Another object of the invention is to provide an oximetry sensor which is relatively inexpensive to manufacture.

A further object of the invention is to provide an oximeter sensor which is universally adaptable for a wide range of finger sizes.

Yet another object of the invention is to provide an oximeter sensor which substantially excludes extraneous light.

A still further object of the invention is to provide an oximeter sensor which can be worn for extended periods without substantial discomfort.

Still another object of the invention is to provide an oximeter sensor which is disposable yet permits expensive components to be reused.

It is another object of the invention to provide an oximeter sensor which substantially reduces the effects of motion artifacts.

These and other objects and advantages of the invention will become apparent from the detailed description thereof taken with the accompanying drawings.

According to one aspect, the invention comprises a non-invasive, disposable oximetry sensor constructed and arranged to be mounted on a patient's tissue. The sensor includes light detecting means for detecting light passing through the tissue at plural wavelengths so that the level of oxygen saturation in the patient's blood can be determined, light emitting means for projecting light onto the patient's tissue for detection of light by the detector, and coupling means for releasably coupling the light emitting means to the sensor whereby the light emitting means may be reused in another sensor when the sensor is discarded.

According to another aspect, the invention comprises a non-invasive, disposable oximetry sensor constructed and arranged to be mounted on a patient's tissue. The sensor includes light detecting means for detecting light passing through the tissue at plural wavelengths so that the level of oxygen saturation in the patient's blood can be determined, light emitting means for projecting light onto the patient's tissue for detection of light by the detector, and coupling means for releasably mounting the light emitting means on the sensor whereby said light emitting means may be reused in another sensor when the sensor is discarded.

According to another aspect, the invention comprises an oximetry sensor constructed and arranged to be mounted on a patient's digit and including first means for engaging the other side thereof, and coupling means for coupling the first and second means for sliding linear engagement toward and away from the opposite sides of the digit and for preventing separation thereof, at least one light projecting means disposed on one of the first and second means and a light detector on the other of the first and second means for detecting light transmitting through said digit.

According to another aspect, the invention comprises an oximetry sensor constructed and arranged to be attached to a patient's digit and including first means for engaging one side of the digit and second means for engaging the other side thereof, and coupling means for securing the first and second means to the opposite sides of the digit and for resisting separation thereof, at least one light projecting means coupled to one of the first and second means and a light detector mounted on the other of the first and second means for detecting light transmitting through the digit. The coupling means includes first and second ratchet means mounted on the first and second means, respectively, the first and second ratchet means being engageable upon movement of said first and second means in a first direction toward each other, the first and second ratchet means being respectively arranged to permit relative sliding movement in said first direction and to inhibit movement in the opposite direction, and release means formed on one of the first and second means to facilitate manual disengagement of one of the first and second ratchet means to thereby permit separation of the first means from said second means so that said sensor may be removed from the digit.

According to another aspect, the invention comprises a non-invasive, disposable oximetry sensor constructed and arranged to be mounted on a patient's tissue. The sensor includes light detecting means for detecting light passing through the tissue at plural wavelengths so that the level of oxygen saturation in the patient's blood can be determined, light emitting means for projecting light onto the patient's tissue for detection of light by the detector, one of the light detecting means and light emitting means being spaced form the sensor, light transmitting for transmitting light between the spaced light detecting or emitting means to the sensor, and coupling means for releasably coupling the light transmitting means to the sensor whereby said light emitting or detecting means may be reused in another sensor when said sensor is discarded.

BRIEF DESCRIPTION OF THE DRAWINGS

FIG. 1 shows an oximetry sensor illustrating one embodiment of the invention;

FIG. 2 shows a cross section of the oximetry module illustrated in FIG. 1;

FIGS. 3 and 4 show an oximetry sensor embodying an alternate embodiment of the invention;

FIG. 5 shows an oximetry sensor illustrating a further embodiment of the invention.

FIG. 6 is a perspective view of an alternate embodiment of oximeter probe illustrating the invention;

FIG. 7 is an exploded view of the oximeter probe shown in FIG. 6;

FIG. 10 is a plan view of a portion of the oximeter probe shown in FIG. 6;

FIG. 11 is a front view of the oximeter probe shown in FIG. 6; and

DETAILED DESCRIPTION OF THE PREFERRED EMBODIMENT

Figure 8:
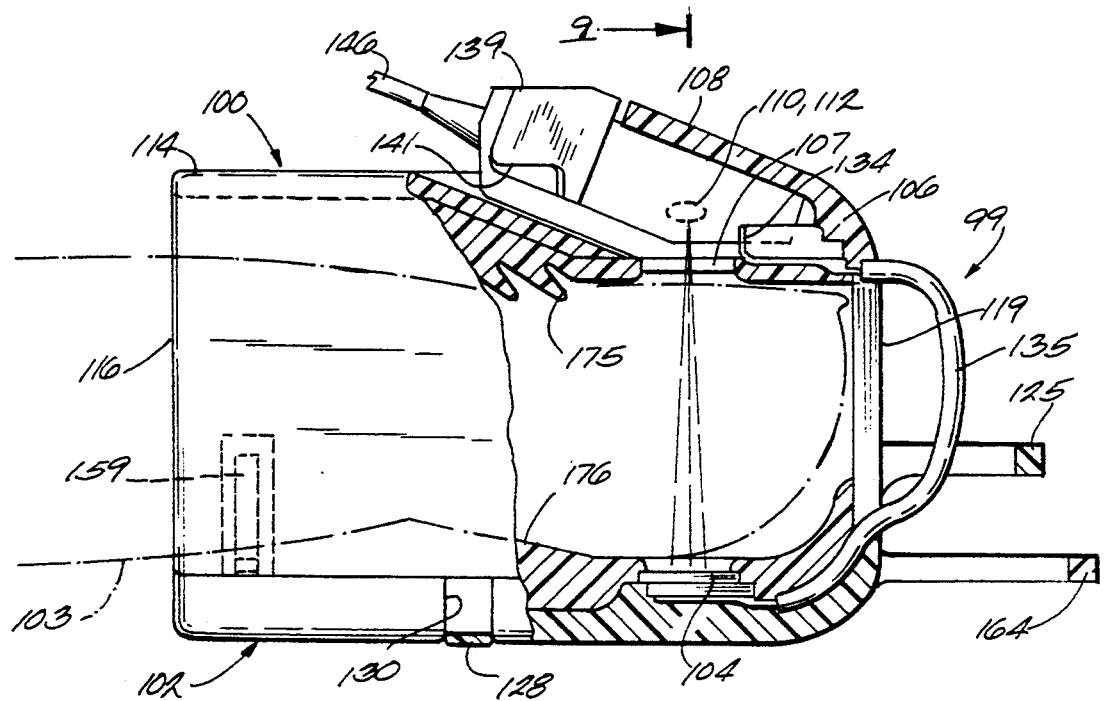
FIG. 8 is a view taken along lines 8—8 of FIG. 6.
Figure 9:
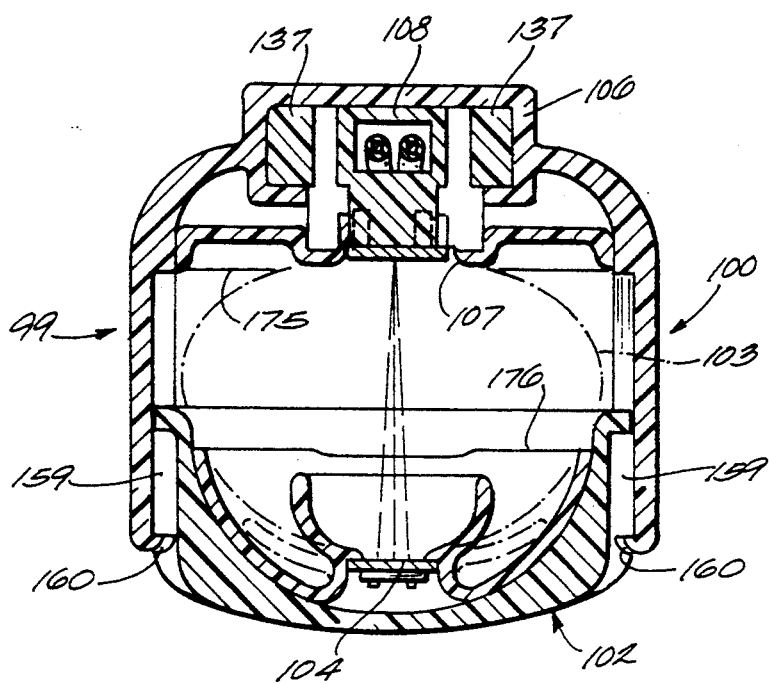
FIG. 9 is a view taken along lines 9—9 of FIG. 8.

FIG. 1 shows a first embodiment of an oximetry sensor 10 illustrating the invention and including an open-ended, hollow first shell 11 and a second shell member 12 which are joined at one end by a flexible strap 14. The members 11 and 12 and the flexible strap 14 are preferably formed of any suitable plastic material, such as polyvinylchloride.

The shell member 11 is open-ended and is defined by a top wall 16 which diverges outwardly at a slight angle from front to rear and side walls 18 and 19 depending from top wall 16. The inner surface 21 of the member 11 is arcuate in transverse section and also diverges slightly from front to back to conform generally to the shape of a human finger. An inverted, generally U-shaped opening 22 is formed centrally in each of the sidewalls 17 and 18. On the inner surface of each sidewall 17 and 18 and on each of the opposite sides of the openings 22 there are a row of vertically arrayed teeth 24. The lower surface 26 of each tooth 24 is inclined upwardly and the upper surface 27 thereof is generally horizontal.

Shell member 12 is also generally U-shaped in transverse section and includes a bottom wall 30 and side walls 31 and 32, all of which are sized and configured to be received between the side walls 18 and 19 of body 11. Member 12 also tapers slightly from front to rear similar to the body member 11 and includes an inner surface 34 complementary to the surface 21. A pressure pad 36 extends laterally from each side wall 31 and 32 and each is complementary to and is positioned to be received within the openings 22 in member 11 when the member 12 is in its closed position as shown by broken lines in FIG. 1. Disposed on the outer surfaces of side walls 31 and 32 and adjacent the sides of each pressure pad 36 are a vertical row of teeth 38 which are complementary to the teeth 24 in body 11 and each has an inclined upper surface 39 and a generally horizontal lower surface 40. The flexible strip 14 extends between the front ends of the upper wall 16 of body 11 and the lower wall 30 of closure member 12.

A pair of LEDs 43 and 44 are mounted in the upper wall 16 of body 11 and face downwardly for respectively transmitting red and infrared light onto a finger disposed between the body 11 and closure member 12. A detector 45 is disposed in the closure member 12 and faces upwardly in an opposed relation to the LEDs 43 and 44. Conductors 48, 49 and 50 respectively connect the LEDs 43 and 44 and the detector 45 to a terminal 52 in the upper wall 16 of body 11. An additional conduct (not shown) connects the terminal 52 to a detector (not shown) in the closure member 12. A cable 54 has a terminal 56 on one end for mating with the terminal 52. The other end of cable 54 is connected to a control and processing unit (not shown) which is operative to alternately energize the LEDs 43 and 44 and for receiving the voltage signals generated by the detector 45, which are functionally related to the light passing through the patient's finger. The processor and control (not shown) uses these voltage signals for calculating the oxygen saturation level of the patient's blood in a manner well-known in the art.

In mounting the sensor on the patient's finger, the first member 11 is first placed on the upper surface of the finger and the second member 12 is then pivoted upwardly with the pressure pads 36 passing into the openings 22. The configuration of the teeth 24 and 38 will permit the teeth 38 to ratchet upwardly over the teeth 24. Because of the shape of the teeth, the teeth 38 will be prevented from moving downwardly relative to the teeth 24 by the interaction of the surfaces 27 and 40. The patient's finger will thus be captured between the members 11 and 12. Because the ratcheting action of teeth 24 and 38, the LEDs 43 and 44 and the detector 45 can be positioned closely on the opposite side of a large range of finger sizes. As a result, the sensor 10 is self-adjusting. In addition, because the finger is closed on all sizes by the men, hers 11 and 12, little ambient light will penetrate to the detector 45. Also, because the closure men%her 12 is held in position by the teeth 24 and 38, rather than by a spring action, there is little, if any, discomfort to the patient even when the sensor 10 is worn for long periods.

When it is desired to remove the sensor 10 from the patient's finger, the pressure pads 36 are pressed inwardly by the thumb and forefinger, which separates the teeth 38 from the teeth 24. This permits the men%her 12 to pivot downwardly from its closed position shown by broken lines to its position shown by full lines in FIG. 1.

FIGS. 3 and 4 show an alternate embodiment of a sensor 60 according to the invention and which also includes a first shell member 61, a second shell member 62, and a connecting strap 64. The first and second member 61 and 62 are configured substantially the same as members 11 and 12 of the embodiment of FIGS. 1 and 2, except for the manner in which they are locked together and released. In the embodiment of FIG. 3, there are a pair of generally vertical spaced apart slits 65 extending upwardly from the lower edge of each side wall 66 and 67 of body member 61 to define flaps 69. On the inner surface of each flap 69, there is a vertically oriented row of teeth 71 configured similarly to the teeth 24 of FIG. 1. In addition, on the outer surface of each of the side walls 73 of the closure member 62, there is a row of complementary teeth 76. On the lower edge of the flap 69, a finger tab 78 may be formed. The sensor 61 also includes LEDs 43 and 44 and a detector 45, all arranged and electrically connected to a socket 52 in the manner discussed with respect to FIG. 1.

It will be appreciated that the sensor 61 can be attached to a patient's finger in the same manner as the embodiment of FIGS. 1 and 2. In particular, the teeth 76 ratchet over the teeth 71 as the second member 62 is moved toward the first member 61. This will hold the sensor 60 on the patient's finger without undue pressure and is self-adjusting for fingers of various sizes. Moreover, the configuration of the members 61 and 62 substantially excludes ambient light from the detector 45. The second member 62 may be released by pulling outwardly on the flaps 69 to move the teeth 71 away from the teeth 76 as shown in FIG. 4.

A further embodiment of the invention is shown in FIG. 5. Here, the first shell member 18 and the second shell member 12 are the same as that shown in FIGS. 1 and 2, although other variations of these members are also contemplated. In addition, a detector 45 is disposed in the body member 12. However, the LEDs 80 and 82 are disposed in a separate module 83. A fiber optic cable or light pipe 84 is connected at one end to the module 83 and is connected to the first shell member 12 in any suitable manner. For example, a quick disconnect plug or optical coupler 86 may be mounted on the fiber optic cable 84 and is receivable in a receptacle 87 formed in the upper surface of the top wall 16. The plug or optical coupler 86 receives light from the cable or light pipe 84 and projects the same downwardly through an opening 89 in receptacle 87 and is toward the detector 45. At the other end of the cable or light pipe 84, there is a light collector 90 which is oriented to receive light from the LEDs 80 and 82. The module 83 is connected by a cable 92 to a processor control and display 94 which is well-known in the art and is operative to alternately energize the LEDs 80 and 82 and to calculate and display the oximetry value from the light detected at each wavelength by detector 45. Also mounted on the fiber optic cable is an electrical conductor (not shown) for coupling the detector 45 to the module 83.

After the sensor 10 has been attached to the patient's finger in the manner discussed with respect to FIGS. 1 and 2, the oximeter processor and control 94 alternately energizes the LEDs 80 and 82, one of which emits light in the red band width and the other in the infrared band width. This light is transmitted along the fiber optic cable to the end 88, where it is projected downwardly through the patient's finger with the unabsorbed portion being detected by the detector 45.

The sensor 10, as shown in FIG. 5, can be disposable, while the module 83 is retained. Since the LEDs 80 and 82 are not discarded along with the sensor 10, they can be dedicated to the oximeter processor and control 94. As a result, the coefficients for the specific wavelengths of light emitted by the LEDs 80 and 82 can be inserted directly into the Lambert-Beers equation contained in the processor's software. For this reason, there is no necessity for the processor's memory to include a look-up table, nor is a coding resistor necessary in the sensor.

FIGS. 6-11 illustrate an oximeter sensor 99 including a preferred embodiment of the invention. The sensor 99 include an upper shell member 100 and a complementary lower shell member 102 which is slidably received within the upper shell member 100 to define a housing which is open at one end for receiving a patient's finger 103 as shown in FIG. 8. A detector 104 is mounted in the lower shell member 102. A receptacle 106 is formed on the upper shell 102 and positioned about an opening 107 which is positioned in alignment with the detector 104. A plug 108 is constructed and arranged to be received within the receptacle 106 and includes a pair of LEDs 110 and 112 (FIG. 10) positioned such that when the plug 108 is within the receptacle 106, the LEDs 110, 112 are positioned above the opening 107 and hence are in alignment with the detector 104 so that light rays emitted from the LEDs 110 and 112 and passing through the patients finger 103 will be received by the detector 104.

The shell members 100 and 102 may have any suitable shape which will cover the tip of the patient's finger. In the illustrated embodiment, shell member 100 includes a top wall 114, a pair of depending side walls 116 and 117 and a front wall 119 (FIG. 11). A pair of vertically oriented, spaced apart grooves 121 and 122 are formed on the inner surface of each of the side walls 116 and 117. In addition, there is a rectangular opening 124 formed in the front wall 119 and a generally U-shaped forwardly extending gripper 125 which engages the front wall 119 in the opposite sides of the opening 124. An anchor 126 is formed in the upper center of each side wall 116 and 117 and generally is displaced inwardly for receiving the shaped ends 127 of an elastic band 128 which is formed of a rubber or rubber-like material. The band 128 extends downwardly along a first groove 129 on the inner surface of each side wall 116 and 117 and around a second groove 130 formed in the lower shell 102. This resiliently biases the shells 100 and 102 toward a closed position to retain the sensor 99 on the patient's finger without exerting undue pressure which would cause discomfort if the probe is worn for extended periods.

The receptacle 106 includes a hood 131 formed over a slot 132 to define a tapered recess 133 for receiving the plug 108. At the inner end of the recess 133 there are a pair of contacts 134 coupled by a lead 135 to the detector 104.

The plug 108 is shaped to be received within the recess 133 and includes a pair of rearwardly extending, integral spring arms 137 each having a finger grip 139 at its outer end. A catch 141 formed on each finger grip 139 is engageable with a latch 143 formed on each side of the shell 129 to retain the plug 108 in position. The plug 108 may be released by pushing inwardly on the arms 137 to move the catches 141 inwardly and away from the latches 143. A pair of contacts 145 mounted at the forward end of plug 108 are engageable with the contacts 134 disposed within the recess 132 when the plug 108 is latched in position. Plug 108 is mounted on a cable 146 having conductors (not shown) which connect to the contacts 145 and to the LEDs 110 and 112. The other end of cable 146 carries a plug (not shown) for connecting the cable to an oximeter module.

The lower shell member 102 includes a bottom wall 150 which is slightly arched, a pair of side walls 152 and 153 and a front wall 155. On each side wall 152 and 153 there are pair of guide rails 157 and 158 which are sized and spaced apart to be slidably receivable respectively within the grooves 121 and 122 formed on the inner surfaces of side walls 116 and 117 of shell member 100. Each of the rails 157 and 158 has a longitudinal central groove 159 for receiving a stop member 160 disposed in lower end of each of grooves 121 and 122. AS the members 10 and 102 are moved away from each other, the stop members 160 will be moved in the grooves 159 until they engage the upper ends thereof in which case further movement will be prevented. Similarly, movement of the members 100 and 102 toward each other is limited by the engagement of the ends 162 of the guide rails 157 and 158 with the upper ends of grooves 121 and 122.

At the front of the second shell member 102 there is an integral, U-shaped finger grip 164 and a pair of forwardly extending guide rails 166 which engage the edges of the opening 124.

The pair of soft pads 175 and 176 are disposed, respectively, within the shells 100 and 102 for engaging the opposite sides of a patient's finger when the shells are moved toward each other. While the pads 175 and 176 may take any conventional form, in the preferred embodiment they are shown to have a relatively smooth, dished surface. Each pad 175 and 176 has an opening 178 and 179 respectively to permit light rays to pass form the LEDs 110 and 112 to the detector 104.

In operation, the shells 100 and 102 and first separated against the biasing force of the band 128 to permit the patient's finger to be inserted. The frictional force between the members will be sufficient to hold them apart, After the patients finger has been inserted, the shells are pushed toward each other until the pads engage the finger snugly but without discomfort. As the shell members 100 and 102 are moved toward each other, the finger grip 164 will move upwardly and away from the grip 125. When it is desired to remove the sensor 99 from the patient's finger, the operator exerts pressure on the finger grips 125 and 164 which moves the lower shell 102 away from the upper shell 100.

The grooves 21 and 22 and the guide rails 157 and 158 insure that the LEDs 110 and 112 remain in alignment with the detector 104 as the shells 100 and 102 are moved toward and away from each other. This is also aided by the engagement of the guide rails 166 engaging the edges of the opening 124.

It would be appreciated that by mounting the LEDs 110 and 112 and a plug 108 which is removable from the probe 99, the relatively more expensive LEDs can be reused notwithstanding that the remaining portions o#the probe 99 are disposable.

Figure 12:
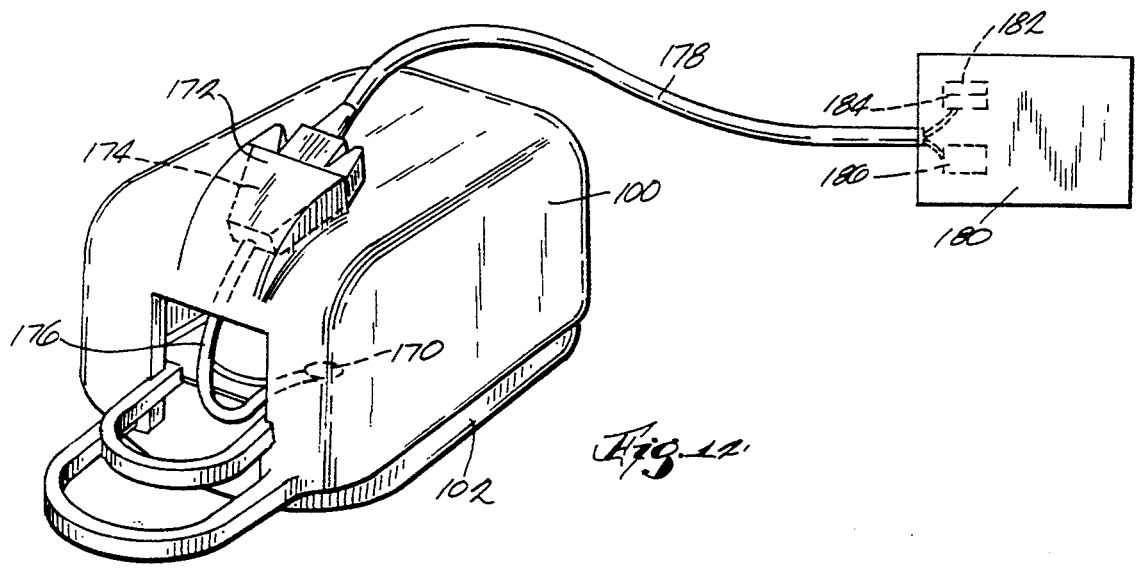
FIG. 12 is a perspective view of an alternate embodiment of the invention.

A further embodiment of the invention is shown in FIG. 12. Here the shells 100 and 102 are the same as in FIGS. 6–11. However, the detector has been replaced by a light collector 170 and the plug 172 and socket 174 comprise an optical coupler. A first fiber optic cable 176 connects the light collector 170 to the optical coupler 172, 174 and a second fiber optic cable 178 connects the coupler to a module 180 which contains a pair of LEDs 182, 184 and a detector 186. Light generated by the LEDs 182, 184 is transmitted through the fiber optic cable 178 to the light coupler and thence it is transmitted downwardly through the patient's finger where a portion is received by the collector 170. This received light is transmitted through the fiber optic cable 176 to the optic coupler and then through the fiber optic cable 178 to the detector within module 180. This permits the shells 100 and 102 to be discarded while the LED's 182 and 184 and the detector 186 are retained.

While only a few embodiments of the invention have been illustrated and described, it is not intended to be limited thereby but only by the scope o#the appended claims.

We claim:

1. A non-invasive, disposable oximetry sensor including first and second shell members, first coupling means for coupling said first and second shell members and including guide means on said first and second shell members for guiding said first and second shell members for linear movement toward and away from each other, said shell members being constructed and arranged to receive a patient's tissue therebetween and for being supported by the patient's tissue, said sensor including light emitting means mounted on said first shell member for projecting light into the patient's tissue, light detecting means mounted on said second shell member in a predetermined alignment with said light emitting means for detecting light projecting through the tissue so that the level of oxygen saturation in the patient blood can be determined, and second coupling means for releasably mounting said light emitting means on said first shell member in the predetermined alignment position relative to said light detecting means whereby said light emitting means may be reused in another sensor when said sensor is discarded, the linear movement of said first and second shell member maintaining the alignment of said light detecting means and said light emitting means as said first and second shell member are moved toward and away from each other and for preventing misalignment thereof.

2. The oximetry sensor set forth in claim 1 wherein said second coupling means including plug and a receptacle disposed on said sensor for receiving said plug, said light emitting means being mounted on said plug.

3. The oximetry sensor set forth in claim 2 and including resilient means for releasably holding said plug in said receptacle.

4. The oximetry sensor set forth in claim 1 wherein said first shell member is constructed and arranged to engage one said of a patient's digit and said first shell member is constructed and arranged to engage one side of a patient's digit and said second shell member is constructed and arranged to engage the opposite side thereof.

5. The oximetry sensor set forth in claim 4 wherein said second coupling means includes a plug and a receptacle disposed on said second shell member for receiving said plug, said light emitting means being mounted on said plug.

6. The oximetry sensor set forth in claim 5 wherein said receptacle has a first contact disposed therein and said plug has a second contact thereon for engaging said first contact when said plug is within said receptacle, and conductor means for connecting said first contact to said light detecting means.

7. The oximetry sensor set forth in claim 6 wherein each of said shell members has side walls which are moveable in a generally parallel relation when the first and second shell members are moved toward or away from each other, each of said shell members having an inner surface which is arcuate in transverse section for defining a cavity conforming generally to the opposites sides of a human finger, movement of said shell members toward each other adjusting the size of said cavity without altering the alignment of said light detecting mean sand said light emitting means.

8. An oximetry sensor constructed and arranged to be mounted on a patient's digit and including a first shell member for engaging one side of the digit and a second shell member for engaging the other side thereof and for being supported thereon, coupling means for coupling said first and second shell members to define a cavity for receiving a patient's digit, said coupling means including guide means on said first and second shell members for guiding said first and second shell members for linear movement and away from the opposite sides of the digit for adjusting the size of the cavity, at least one light projecting means disposed on the first shell member for projecting light into said digit and a light detecting means disposed on the second shell portion with a predetermined orientation relative to said light projecting means for detecting light transmitted through said digit, the linear movement of said first and second shell members maintaining the orientation of said light projecting means and said light detecting means as said first and second shell members are moved toward and away from each other as said sensor is adapted to be mounted on a patient's digit and regardless of the relative size of the digit.

9. The oxygen sensor set forth in claim 8 wherein said second shell member is slideably mounted on said first shell member for movement toward and away from each other, the guide means including rail means on said first and second shell members for maintaining said light projecting means and said light detecting means in alignment as said first and second shell members are moved toward and away from each other.

10. The oxygen sensor set forth in claim 9 wherein said rail means comprises first and second parallel spaced apart rails, and including resilient means coupled to said first and second shell members between said rails for urging the shell members toward each other with uniform pressure.

11. The oxygen sensor set forth in claim 8 and including means for releasably coupling said light projecting means to one of said first and second shell members so that said light projecting means may be retained for use on another sensor when said sensor is discarded.

12. A noninvasive, disposable oximetry sensor including first and second members constructed and arranged to be mounted on the opposite sides of a patient's digit and to be supported thereby, coupling means on said first and second members for guiding said members for linear movement toward and away from each other to facilitate mounting said sensor on a patient and to accommodate different size digits, light emitting means mounted on one of said members for projecting light onto the patient's tissue, light detecting means mounted on the other of said members for detecting light passing through the digit so that the level of oxygen saturation in the patient's blood can be determined, said light emitting means and said light detecting means having a predetermined orientation to each other, said coupling means including guide means disposed on said first and second members for guiding said portions for linear relative movement so that said light emitting means and said light detecting means move linearly toward and away from each other to maintain the predetermined orientation of said light emitting means and said light detecting means as said portions are displaced toward or away from each other.

13. The oximetry sensor set forth in claim 12 wherein said light emitting means is spaced form said sensor, and light transmitting means for transmitting light between said spaced light emitting means and said sensor, and coupling means for releasably coupling said light emitting means to said sensor whereby said light emitting means may be reused in another sensor when said sensor is discarded.

14. The oximetry sensor set forth in claim 13 and including a plug, a receptacle disposed in one of said shell members for receiving said plug, said light emitting means being coupled by said light transmitting means to said plug.

15. An oximetry sensor constructed and arranged to be attached to a patient's digit and including a first shell member for engaging one side of the digit and a second shell member for engaging the other side thereof, and coupling means for coupling said first and second members for relative sliding movement toward and away from each other, light projecting means coupled to said first shell member for projecting light onto said digit, light detecting means mounted on said second shell member and in general alignment with said light projecting means for detecting light transmitted through the digit, said coupling means including linear guide means mounted on said first and second shell members for guiding said shell members linearly toward and away from each other to maintain the alignment between the light transmitting means and said light detecting means regardless of the size of the digit and during movement of the shell portions toward or away from each other.

16. The oximetry sensor set forth in claim 15 wherein each of said shell members has a sidewall which is moveable in a generally parallel relation to the side wall on the other shell member when the first and second shell members are moved, and a guide rail formed on one of said shell members and a guide formed on the other shell member and engageable with said guide rail on the other one shell member, said guide rail extending in the direction of movement of said shell members to maintain the alignment between the light projecting means and the light detecting means as said shell members are moved.

17. The oximetry sensor set forth in claim 16 wherein there are a pair of parallel spaced apart guide rails on the first shell member and a pair of parallel spaced apart guides on the second shell member and resilient means coupled to said first and second shell members between said rails for urging said shell members toward each other.

18. A non-invasive, disposable oximetry sensor constructed and arranged to be mounted on and supported by a patient's tissue, said sensor including first and second members for receiving a patient's tissue therebetween, light emitting means for projecting light onto the patient's tissue, light detecting means mounted on the second member in a fixed predetermined position for detecting light from said light emitting means and passing through the tissue so that the level of oxygen saturation in the patient's blood can be determined, a receptacle mounted in a predetermined position on said first member and aligned with said detecting means and a plug releasably coupled to said receptacle, resilient means mounted on said plug and engageable with said receptacle for releasably holding said plug in said receptacle, said light emitting means being coupled to said plug for projecting light through said tissue and ont said detecting means, said plug and receptacle permitting said light emitting means to be coupled to and uncoupled from said first member and reused in another sensor when said sensor is discarded, the coupling of said plug in said receptacle being operative to position said light emitting means in a fixed predetermined alignment relative to said detecting means, said receptacle having first contact means disposed therein and said plug having second contact means thereon engaging said first contact means when said plug is within said receptacle and aligned with said detecting means.

19. The oximetry sensor set forth in claim 18 wherein said light emitting means is mounted in said plug for being releasably mounted on said sensor.

20. The oximetry sensor set forth in claim 19 wherein said light emitting is spaced from said sensor and including light transmitting means for transmitting light from said light emitting means to said sensor, said light transmitting means being coupled to said plug means.

* * * * *

UNITED STATES PATENT AND TRADEMARK OFFICE
CERTIFICATE OF CORRECTION

PATENT NO. : 5,339,810

DATED : August 23, 1994

INVENTOR(S) : David L. Ivers and Stanley R. Mach

It is certified that error appears in the above-identified patent and that said Letters Patent is hereby corrected as shown below:

Column 8, line 42 "member" should be --members--.

Column 9, line 11 "mean sand" should be --means and--.

Column 9, line 21 after "movement" and before "and" insert --toward--.

Column 10, line 10 "form" should be --from--.

Column 10, line 48 after "the" and before "one" delete --other--.

Column 12, line 13 after "plug" delete --means--.

Signed and Sealed this

Second Day of May, 1995

Attest:

BRUCE LEHMAN

Attesting Officer

Commissioner of Patents and Trademarks